United States Patent [19]
Casey et al.

[11] Patent Number: 6,004,968
[45] Date of Patent: Dec. 21, 1999

[54] PHARMACEUTICAL COMPOSITIONS CONTAINING LAMIVUDINE

[75] Inventors: Warren Michael Casey, Knightdale; Ngoc-Anh Thi Nguyen, Durham, both of N.C.

[73] Assignee: Glaxo Wellcome Inc., Research Triangle Park, N.C.

[21] Appl. No.: 09/044,896

[22] Filed: Mar. 20, 1998

Related U.S. Application Data

[60] Provisional application No. 60/042,353, Mar. 24, 1997.

[30] Foreign Application Priority Data

Mar. 26, 1997 [GB] United Kingdom .................... 9706295

[51] Int. Cl.⁶ .................................................. A61K 31/505
[52] U.S. Cl. ............................................... 514/274
[58] Field of Search ............................................ 514/274

[56] References Cited

U.S. PATENT DOCUMENTS

| | | | |
|---|---|---|---|
| 5,047,407 | 9/1991 | Belleau et al. | 514/274 |
| 5,859,021 | 1/1999 | Cameron et al. | 514/274 |

FOREIGN PATENT DOCUMENTS

| | | |
|---|---|---|
| 96/26734 | 9/1996 | WIPO . |
| 96/30025 | 10/1996 | WIPO . |
| 97/33565 | 9/1997 | WIPO . |

OTHER PUBLICATIONS

Casey et al., J. Pharmaceutical Science and Technology, 50(6), 352–355, Nov. 12, 1996.

Nguyen et al., Drug Development and Industrial Pharmacy, 21(14), 1671–1682, Jul. 1995.

Warren M. Casey, et. al., "Use of the Green Fluorescent Protein to Rapidly Access Viability of *E coli* Preserved Resolutions," *PDA Journal of Pharmaceutical Science & Technology*, vol. 50, No. 6 / Nov.–Dec. 1996, pp. 352–355.

Mickey L. Wells, et., al., "Formulation of a Preservative System Using Pass/Fail Data," PT 6177, *Pharmaceutical Research*, 10(10) S171 (1993).

Warren M. Casey, et al., "Use of the Green Fluorescent Protein to Rapidly Assess Viability of *E coli* Preserved Resolutions," PDA (International Association for Pharmaceutical Science and Technology) 1996 Annual Meeting Courses, and Exhibit, Pharmaceutical Manufacturing & Technology: Past, Present & Future, Nov. 18–22, 1996, Phila., PA, pp. 18–19.

Ngoc–Anh T. Nguyen, et. al., "Identification of Factors Affecting Preservative Efficacy and Chemical Stability of Lamivudine Oral Solution Through Statistical Experimental Design," *Drug Development and Industrial Pharmacy*, 21(14), pp. 1671–1682 (1995).

*Primary Examiner*—Phyllis G. Spivack
*Attorney, Agent, or Firm*—Karen L. Prus

[57] ABSTRACT

The present invention relates to pharmaceutical formulations containing (2R, cis)-4-amino-1-(2-hydroxymethyl-1,3-oxathiolan-5-yl)-(1H)-pyrimidin-2-one (−)-2′,3′-dideoxy,3′-thiacytidine, lamivudine, that are substantially free of ethanol and ethylenediamine-tetraacitic acid, and their use in medical therapy.

12 Claims, 1 Drawing Sheet

PHARMACEUTICAL COMPOSITIONS CONTAINING LAMIVUDINE

This application claims priority to U.S. 60/042,353 filed Mar. 24, 1997 and GB 9706295.4 filed Mar. 26, 1997.

FIELD OF THE INVENTION

The present invention relates to novel pharmaceutical compositions containing (2R, cis)-4-amino-1-(2-hydroxymethyl-1,3-oxathiolan-5-yl)-(1H)-pyrimidin-2-one ((-)-2',3'-dideoxy,3'-thiacytidine, Epivir®, lamivudine) and their use in medical therapy.

BACKGROUND OF THE INVENTION

Retroviruses form a sub-group of RNA viruses which, in order to replicate, must first "reverse transcribe" the RNA of their genome into DNA ("transcription" conventionally describes the synthesis of RNA from DNA). Once in the form of DNA, the viral genome may be incorporated into the host cell genome, allowing it to take advantage of the host cell's transcription/translation machinery for the purposes of replication. Once incorporated, the viral DNA is virtually indistinguishable from the host's DNA and, in this state, the virus may persist for the life of the cell.

A species of retrovirus, the Human immunodeficiency virus (HIV) has been reproducibly isolated from patients with AIDS (acquired immunodeficiency syndrome) or with the symptoms that frequently precede AIDS. AIDS is an immunosuppressive or immunodestructive disease that predisposes subjects to fatal opportunistic infections. Characteristically, AIDS is associated with a progressive depletion of T-cells, especially the helper-inducer subset bearing the CD4 surface marker. HIV is cytopathic and appears to preferentially infect and destroy T-cells bearing the CD4 marker, and it is now generally recognized that HIV is the etiological agent of AIDS. Clinical conditions such as AIDS-related complex (ARC), progressive generalized lymphadenopathy (PGL), Karposi's sarcoma, thrombocytopenic purpura, AIDS-related neurological conditions, such as AIDS dementia complex, multiple sclerosis or tropical paraparesis, and also anti-HIV antibody-positive and HIV-positive conditions, including such conditions in asymptomatic patients, are also conditions which may be treated by appropriate anti-viral therapy.

Another RNA virus which has been recognized as the causative agent of an increasingly serious international health problem is the non-A, non-B hepatitis virus. At least 80% of cases of chronic post-transfusional non-A, non-B hepatitis have been shown to be due to the virus now identified as hepatitis C and this virus probably accounts for virtually all cases of post-transfusional hepatitis in clinical settings where blood products are screened for hepatitis B. Whereas approximately half of the cases of acute hepatitis C infection resolve spontaneously over a period of months, the remainder become chronic and in many if not all such cases chronic active hepatitis ensues with the potential for cirrhosis and hepatocellular carcinoma. The structure of the hepatitis C virus genome has been elucidated and the virus has been characterized as a single stranded RNA virus with similarities to flaviviruses.

Hepatitis B virus (HBV) is a small DNA containing virus which infects humans. It is a member of the class of closely related viruses known as the hepadnaviruses, each member of which selectively infects either mammalian or avian hosts, such as the woodchuck and the duck. Recent insights into the mechanism of replication of the hepadnavirus genome indicate the importance of reverse transcription of an RNA intermediate, suggesting that the reverse transcriptase is a logical chemotherapeutic target. HBV is a viral pathogen of major world-wide importance. The virus is etiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

U.S. Pat. No. 5,047,407 discloses (2R, cis)-4-amino-1-(2-hydroxymethyl-1,3-oxathiolan-5-yl)-(1H)-pyrimidin-2-one (Epivir®, lamivudine) and its use in the treatment and prophylaxis of viral infections. Lamivudine has proven antiviral activity against HIV and other viruses such as HBV. Current liquid formulations of lamivudine used in the clinic contain disodium(ethylenedinitrilo)tetraacetate dihydrate (edetate disodium, EDTA) and 6% (v/v) ethanol. However, liquid formulations without ethanol or other sedatives and EDTA or other unnecessary anti-oxidants are considered advantageous, particularly for pediatric use and in renally or hepatically impaired adults.

The addition of alcohol and EDTA. is thought to be necessary in order to maintain preservative efficacy against bacteria, yeasts, and mold. EDTA, a chelating agent, has been shown to potentiate the activity of many antimicrobial agents by chelating $Mg^{2+}$ and $Ca^{2+}$ ions which are normally responsible for the stability of the cell wall of Gram-negative organisms. In a study of factors affecting preservative efficacy of lamivudine oral solution, Nguyen et. al. reported that preservative efficacy improved with increasing EDTA concentrations and with increasing pH from 4.5 to 7.5 (Nguyen, N-A. T., et. al., *Drug Development and Industrial Pharmacy* 21, 14, 1671–1682, 1995). The same study reported that the chemical stability of lamivudine increased with increasing pH from 4.5 to 7.5. Preservative efficacy was greatest at pH 7.5, but increasing the pH from 4.5 to 7.5 resulted in extensive degradation of preservatives such as esters of hydroxybenzoate (hereinafter referred to as parabens). All formulations were effective against bacteria and yeasts, but not against the mold, *Aspergillus niger*.

In a study evaluating the effects of alcohol concentration on preservative efficacy of lamivudine oral solution, Wells et. al. reported that the reduction or elimination of alcohol from lamivudine oral solutions resulted in unacceptable preservative efficacy (Wells et al., *Pharmaceutical Research*, 10(10), S171, 1993).

Lamivudine is currently formulated at pH 5.5 with 0.01% EDTA, 0.12% (w/v) methyl paraben, 0.015% propyl paraben, and 6% ethanol. In this formulation, EDTA functions both to maintain pH and preservative efficacy. At this concentration of parabens and pH, ethanol is needed in order to pass the Antimicrobial Preservatives Effectiveness (APE) test according to United States Pharmacopeia (USP) standards (*United States Pharmacopeia* 23, <51>, p. 1681, 1995), BP standards (*Efficacy of Antimicrobial Preservation*, Appendix XVI C, 1995), and PhEur standards (*Efficacy of Antimicrobial Preservation*, Chapter VIII.14, 1992). The pH was maintained at 5.5 in order to preserve the chemical stability of the parabens. We have surprisingly found that there is a sharp increase in preservative efficacy when lamivudine is formulated at pH>5.5 (FIG. 1) and the concentrations of parabens are increased by 20–25% of the concentration of parabens in the ethanol-containing formulation.

We have found that the oral formulations of lamivudine according to the present invention surprisingly maintain preservative efficacy and chemical stability while eliminating ethanol and EDTA.

An object of the present invention is to provide pharmaceutical compositions comprising lamivudine and a preservative system that allows the elimination of ethanol and EDTA, while maintaining preservative efficacy.

SUMMARY OF THE INVENTION

The present invention relates to a pharmaceutical composition, substantially free of ethanol and EDTA, comprising a safe and therapeutically effective amount of lamivudine or a pharmaceutically acceptable derivative thereof and a preservative system comprising parabens in concentrations sufficient to confer and maintain preservative efficacy and a pH of greater than 5.5.

DETAILED DESCRIPTION OF THE INVENTION

Figure 1:
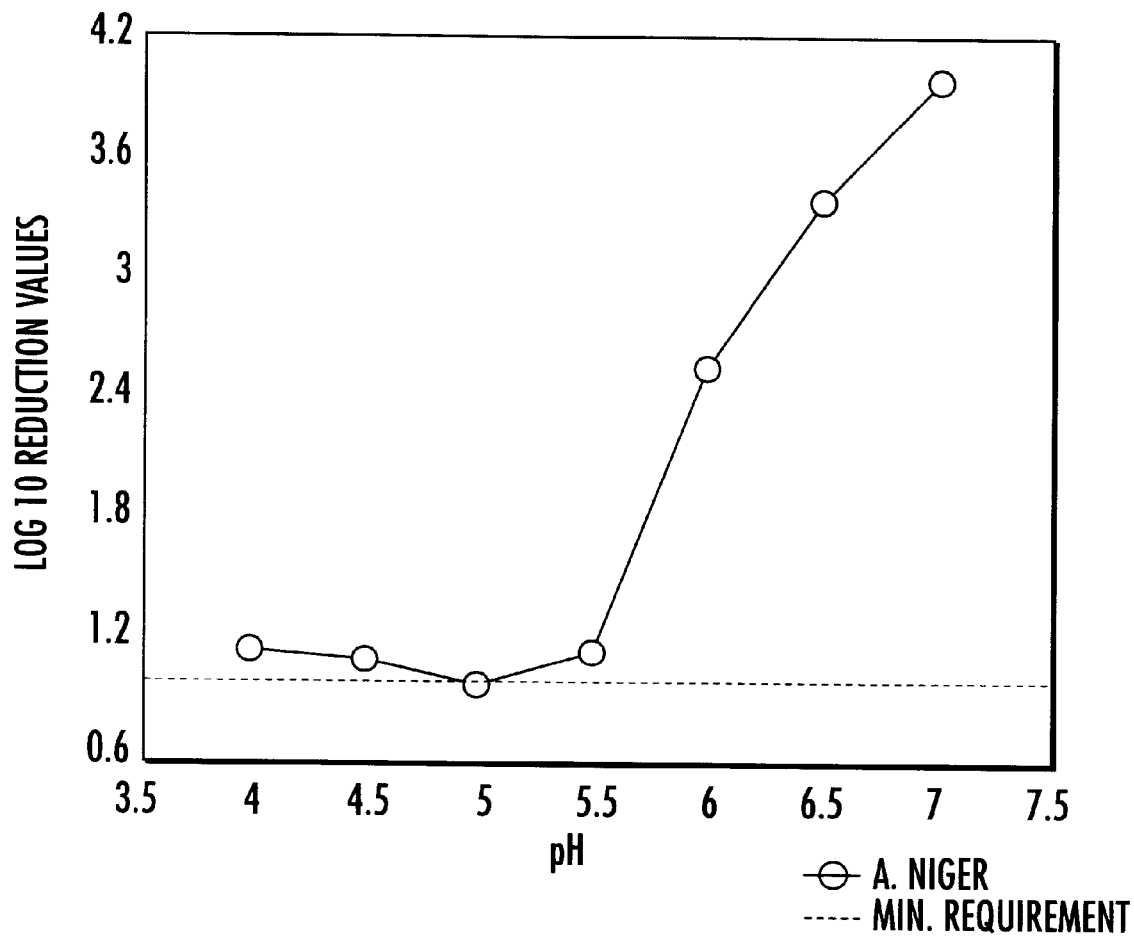
FIG. 1 is a graph of the *Aspergillus niger* in lamivudine oral solution.

The phrase "safe and therapeutically effective amount'" as used herein, means a sufficient amount of a drug, compound, composition, product or pharmaceutical agent to abate or reverse or treat a malady in a human or other mammal without severely harming the tissues of the mammal to which the drug or pharmaceutical agent is administered.

The phrase "pharmaceutically acceptable derivative," as used herein, means any pharmaceutically acceptable salt, solvate, ester, or salt of such ester or any other compound which, upon administration to the recipient, is capable of providing (directly or indirectly) the intended active ingredient or any active metabolite or residue thereof.

The term "substantially free of", as used herein, means present in quantities that have less than a material effect on, or confer less than a material advantage to, the pharmaceutical composition. A pharmaceutical composition substantially free of ethanol may contain, for example, less than 30% ethanol, advantageously 0–1% ethanol. A pharmaceutical composition substantially free of EDTA may contain, for example, less than 0.005% EDTA.

The term "preservative efficacy" or "preservative effectiveness", as used herein, means that the composition satisfies USP standards as defined in protocol <51>, p.1681, *United States Pharmacopeia*, 1995). The preservative is effective in the product examined if (a) the concentrations of viable bacteria are reduced to not more than 0.1% of the initial concentrations by the fourteenth day; (b) the concentrations of viable yeasts and molds remain at or below the initial concentrations during the first 14 days; and (c) the concentration of each test microorganism remains at or below these designated levels during the remainder of the 28-day test period. Similar criteria are defined for BP standards (*Efficacy of Antimicrobial Preservation*, Appendix XVI C, 1995), and PhEur standards (*Efficacy of Antimicrobial Preservation*, Chapter VIII.14, 1992).

The term "preservative system", as used herein, means ingredients and conditions (for example, pH) which result in preservative efficacy.

It will be appreciated by those skilled in the art that reference herein to "treatment" extends to both the prophylaxis and the treatment of an established malady, infection or its symptoms.

The term "EDTA", as used herein, means ethylenediaminetetraacetic acid, and includes disodium EDTA (edetate disodium, (ethylenedinitrilo)tetraacetic acid disodium salt, disodium ethylenediaminetetraacetate), calcium disodium EDTA, sodium iron(III) EDTA, and the like.

The compositions of the present invention employ a safe and therapeutically effective amount of lamivudine or pharmaceutically acceptable salts, solvates and derivatives thereof, together with a safe and effective amount of pharmaceutically acceptable carriers.

According to one aspect of the present invention, there is provided a pharmaceutical composition, substantially free of ethanol and EDTA, comprising lamivudine and parabens, wherein said composition is formulated at pH>5.5.

The pH of the formulation of the present invention may be in the range of 5.56–7.4, advantageously in the range of 5.6–6.5, and most advantageously in the range of 5.8–6.2, particularly about 6.0.

According to the present invention, any ester of hydroxybenzoate (parabens) or combination of such esters may be used, including methyl and propyl paraben and butyl and propyl paraben combinations.

In a further aspect of the present invention, there is provided lamivudine formulations containing methyl paraben and propyl paraben. For oral solutions and suspensions, the range of methyl paraben concentration may be 0.096–0.2% (0.96 mg/mL to 2 mg/mL) and the range of propyl paraben concentration may be 0.01% to 0.02% (0.1 to 0.2 mg/mL).

Advantageously the range of methyl paraben concentration may be 0.15–0.2% (1.5 mg/mL to 2 mg/mL) and the range of propyl paraben concentration may be 0.018% to 0.019% (0.18 to 0.19 mg/mL).

According to a further aspect of the present invention, any suitable buffer may be used to provide a pH>5.5. Advantageously, sodium citrate or phosphate may be used.

The compositions of the present invention may optionally employ diluents, solubilizers, flavoring agents, viscosity-increasing agents (e.g. polyethylene glycol), sweeteners, buffers, or any other excipients commonly used in the art.

Methods for the preparation of lamivudine are described in WO92/20669 and WO95/29174 both incorporated by reference herein.

Included in the invention are the pharmaceutically acceptable salts, esters, or salts of such esters of lamivudine, or any other compound which, upon administration of a safe and therapeutically effective amount of the compound to a human subject, is capable of providing (directly or indirectly) the antivirally active metabolite or residue thereof.

The compositions of the present invention may be formulated using methods and techniques suitable for the compositions' physical and chemical characteristics and that are commonly employed by persons skilled in the art of preparing oral dosage forms (Remington, *The Science and Practice of Pharmacy*, 19th ed., 1995).

The formulations according to the invention may be presented in various forms adapted for direct oral administration including liquid forms, for example, syrups, suspensions, or solutions. The formulations, according to the invention, may include other pharmaceutically acceptable carriers as excipients conventionally used in such formulations. Thus, for example, syrups may include sugar syrup, sorbitol or hydrogenated glucose syrup. Suspensions may include suspending agents such as methylcellulose, microcrystalline cellulose, croscarmellose sodium or dispersible cellulose. Solutions may include sweeteners such as liquid glucose, laevulose, xylitol, maltitol, or lycasin. The formulations may optionally be flavored with artificial or natural flavors.

The formulations include those suitable for oral administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations can be prepared by uniformly and intimately bringing into association the active ingredient with carriers. Formulations of the present invention suitable for oral administration may be presented as a solution or a suspension in an aqueous liquid or a non-aqueous liquid; or as an oil-in-water liquid emulsion or a water-in-oil liquid emulsion.

The formulations of the present invention may be made using methods and techniques that are commonly employed in preparing preparations within the pharmaceutical industry.

In the formulations according to the invention, the amount required of lamivudine will depend upon a number of factors including the severity of the condition to be treated and the age and condition of the recipient and will ultimately be at the discretion of the attendant physician. In general, however, a suitable, effective dose may be in the range of 0.1–20 mg/kg body weight of recipient per day, advantageously 0.1–5 mg/kg/day. The desired dose may preferably presented as one, two, three, four or more sub-doses, for example, containing 0.1–100 mg/mL, advantageously 5–20 mg/mL.

The formulations according to the invention may be used for the treatment or prophylaxis of human retroviral infections including HIV infections, and the consequent clinical conditions resulting from such infections, for example, AIDS, ARC, progressive generalized lymphadenopathy (PGL) and HIV-seropositive and AIDS-antibody-positive conditions.

The formulations according to the invention may be used for the treatment or prophylaxis of human hepatitis B (HBV) infections and the consequent clinical conditions resulting from such infections.

The formulations according to the invention may be employed in medical therapy in combination with other therapeutic agents suitable in the treatment of HIV infections, such as nucleoside reverse transcriptase inhibitors for example zidovudine, zalcitabine, didanosine, stavudine, 5-chloro-2',3'-dideoxy-3'-fluorouridine and (2R, 5S)-5-fluoro-1-[2-(hydroxymethyl)1,3-oxathiolan-5-yl] cytosine, 1592U89; non-nucleoside reverse transcriptase inhibitors for example nevirapine, TIBO, and α-APA; HIV protease inhibitors for example saquinavir, indinavir, ritonavir, 141W94; other anti-HIV agents for example soluble CD4; immune modulators for example interleukin II, erythropoetin, tucaresol; and interferons for example α-interferon.

The formulations according to the present invention may be employed in medical therapy in combination with other therapeutic agents suitable in the treatment of HBV infections, such as α-interferon.

The components of such combination therapy may be administered simultaneously, in either separate or combined formulations or at different times, e.g. sequentially such that a combined effect is achieved.

The following non-limiting examples are included to illustrate the present invention but are not intended to limit the reasonable scope thereof.

EXAMPLE 1

A liquid formulation was prepared as follows:
1) Composition

| Ingredient | Quantity/1000 L Batch |
|---|---|
| Lamivudine* | 10.00 kg |
| Sucrose | 200.0 kg |
| Methyl Hydroxybenzoate | 1.50 kg |
| Propyl Hydroxybenzoate | 180 g |
| Artificial Strawberry Flavor | 800 g |
| Artificial Banana Flavor | 600 g |
| Sodium citrate dihydrate | 11 g |
| Citric acid anhydrous | 1 g |
| Propylene Glycol** | 19.4 L |
| NaOH/HCl, adjust as necessary | pH 6.0 |
| Purified Water | to 1000 L |

*Quantity may be corrected for purity.
**Volume of Propylene Glycol is calculated by weight using the true density of 1.033 g/mL 2) Method of Preparation To an appropriately sized auxiliary vessel, 19.4L of propylene glycol was added. While mixing, 1.50 kg of methyl hydroxybenzoate and 180 g of propyl hydroxybenzoate were added to the propylene glycol and mixed to dissolve. Purified water was dispensed into a stainless steel vessel with an attached mixer. While mixing, the parabens and glycol solution, 200.0 kg sucrose, 1 g citric acid anhydrous, 11 g sodium citrate dihyrate, 800 g artificial strawberry flavor, 600 g artificial banana flavor and 10 kg of lamivudine were added and mixed. A sufficient quantity of purified water to make 201.65 kg was added and mixed. The solution was sampled and the pH was measured and adjusted to pH 6.0. The solution was filtered through a clarifying filter into an appropriately sized receiving vessel.

EXAMPLE 2

Antimicrobial preservative effectiveness testing was performed using the method described in *The United States Pharmacopeia* 23 <51>(1995), United States Pharmacopeial Convention, Rockville, Md., 1994, p. 1681.

Table 1. Antimicrobial Preservative Efficacy Testing Results for Lamivudine 10 mg/mL Ethanol-free Oral Solution (Example 1)
Specifications
Yeast and mold (*A. niger, C. albicans*,): 1 log reduction by day 14, no increase to day 28.
Bacteria: 3 log reduction by day 14, no increase to day 28.
pH 6.0

| Test Organism | Inoculum per mL | Log Reduction at each Incubation Time (days) | | | |
|---|---|---|---|---|---|
| | | 7 | 14 | 21 | 28 |
| *Staphylococcus aureus* | $9.6 \times 10^5$ | 5.50 | 5.98 | 5.98 | 5.98 |
| *Escherichia coli* | $8.0 \times 10^5$ | 5.90 | 5.90 | 5.90 | 5.90 |
| *Pseudomonas aeruginosa* | $1.7 \times 10^5$ | 5.23 | 5.23 | 5.23 | 5.23 |
| *Candida albicans* | $9.6 \times 10^5$ | 3.69 | 5.98 | 5.98 | 5.98 |
| *Aspergillus niger* | $1.4 \times 10^5$ | 4.55 | 5.15 | 5.15 | 5.15 |

EXAMPLE 3

Antimicrobial preservative effectiveness testing was performed using the method described in *The United States*

*Pharmacopeia* 23 <51>(1995), United States Pharmacopeial Convention, Rockville, Md., 1994, p. 1681.

Table 2. 14 Day log reduction values for lamivudine formulations (10 mg/mL).

Specifications

Yeast and mold (*A. niger, C. albicans, Z rouxii*): 1 log reduction by day 14, no increase to day 28.

Bacteria: 3 log reduction by day 14, no increase to day 28.

| pH | m-para | p-para | C. albicans | A. niger | Z. rouxii | S. aureus | E. coli | P. cepacia | P. aeru. |
|---|---|---|---|---|---|---|---|---|---|
| 5.7 | 0.960 | 0.12 | 2.120 | 3.850 | 3.66 | 5.03 | 5.34 | 5.01 | 5.28 |
| 6.3 | 0.960 | 0.12 | 1.980 | 5.230 | 5.04 | 5.15 | 5.04 | 5.19 | 4.98 |
| 5.5 | 1.350 | 0.16 | 5.630** | 5.230 | 5.04 | 5.15 | 5.34 | 5.49 | 4.98 |
| 6.5 | 1.350 | 0.16 | 5.630 | 5.230 | 5.04 | 5.33 | 5.16 | 5.49 | 4.80 |
| 5.5 | 1.440 | 0.16 | 5.630 | 5.230 | 5.04 | 5.15 | 5.34 | 5.49 | 5.28 |
| 6.5 | 1.440 | 0.16 | 5.630 | 5.230 | 5.04 | 5.63 | 5.64 | 5.49 | 4.98 |
| 6.0 | 1.800 | 0.20 | 5.630 | 5.230 | 5.04 | 5.15 | 5.64 | 5.19 | 5.28 |
| 6.0* | 1.800 | 0.20 | 5.630 | 5.230 | 5.04 | 5.63 | 5.64 | 5.19 | 5.28 |
| 5.5 | 1.200 | 0.15 | | 1.36 | | | | | |
| 5.5 | 0.960 | 0.12 | | 0.77 | | | | | |

*Placebo
**Bold numbers represent 100% reduction

What is claimed is:

1. A pharmaceutical composition, substantially free of ethanol and ethylenediaminetetraacetic acid, comprising lamivudine or a pharmaceutically acceptable derivative thereof, and a preservative system.

2. A pharmaceutical composition comprising lamivudine, said composition being substantially free of ethanol and ethylenediaminetetraacetic acid and exhibiting antimicrobial preservative efficacy.

3. A pharmaceutical composition as claimed in claim 2, further comprising parabens, said composition having a pH greater than 5.5.

4. A pharmaceutical composition, substantially free of ethanol and ethylenediaminetetraacetic acid, comprising lamivudine or a pharmaceutically acceptable derivative thereof, methyl paraben, and propyl paraben, said composition having a pH greater than 5.5.

5. A pharmaceutical composition according to claim 4 wherein the concentration of methyl paraben is 0.96 mg/mL to 2 mg/mL and the concentration of propyl paraben is 0.1 mg/mL to 0.2 mg/mL.

6. A pharmaceutical composition according to claim 4 wherein the pH is in the range 5.56–7.4.

7. A pharmaceutical composition according to claim 6 wherein the pH is 6.0.

8. A pharmaceutical composition as claimed in claim 4 wherein the amount of lamivudine is in the range of 0.1–100 mg/mL.

9. A pharmaceutical composition as claimed in claim 8 wherein the amount of lamivudine is in the range of 5–20 mg/mL.

10. A pharmaceutical composition as claimed in claim 4 further comprising a second therapeutic agent.

11. A pharmaceutical composition as claimed in claim 4 for oral administration.

12. A method of treatment of viral infections by administering a pharmaceutically safe and effective amount of a pharmaceutical composition according to claim 4.

* * * * *

UNITED STATES PATENT AND TRADEMARK OFFICE
CERTIFICATE OF CORRECTION

PATENT NO. : 6,004,968

DATED : December 21, 1999

INVENTOR(S) : Casey, Warren Michael, et. al.

It is certified that error appears in the above-identified patent and that said Letters Patent is hereby corrected as shown below:

In Column 3, Line 37, wherein it reads: "30% ethanol, " change to --3% ethanol, --

Signed and Sealed this

Twenty-seventh Day of March, 2001

Attest:

NICHOLAS P. GODICI

Attesting Officer

Acting Director of the United States Patent and Trademark Office